United States Patent
Kim et al.

(10) Patent No.: US 10,143,363 B2
(45) Date of Patent: Dec. 4, 2018

(54) ENDOSCOPIC INSTRUMENT

(71) Applicants: Ki Bong Kim, Seoul (KR); Jay Bong Kark, Seoul (KR)

(72) Inventors: Ki Bong Kim, Seoul (KR); Jay Bong Kark, Seoul (KR)

( * ) Notice: Subject to any disclaimer, the term of this patent is extended or adjusted under 35 U.S.C. 154(b) by 638 days.

(21) Appl. No.: 14/700,670

(22) Filed: Apr. 30, 2015

(65) Prior Publication Data
US 2016/0317001 A1 Nov. 3, 2016

(51) Int. Cl.
| A61B 1/00 | (2006.01) |
| A61B 1/018 | (2006.01) |
| A61B 18/24 | (2006.01) |
| A61B 18/00 | (2006.01) |
| A61B 18/22 | (2006.01) |

(52) U.S. Cl.
CPC .......... *A61B 1/018* (2013.01); *A61B 1/00177* (2013.01); *A61B 1/00179* (2013.01); *A61B 18/24* (2013.01); *A61B 2018/00982* (2013.01); *A61B 2018/2272* (2013.01)

(58) Field of Classification Search
CPC ....... A61B 1/018; A61B 1/05; A61B 1/00177; A61B 1/00179; A61B 1/00098; A61B 18/24; A61B 2018/00982; A61B 2018/2272
See application file for complete search history.

(56) References Cited

U.S. PATENT DOCUMENTS

| 4,190,041 A * | 2/1980 | Chikama | A61B 1/00098 600/104 |
| 5,309,895 A * | 5/1994 | Yabe | A61B 1/05 348/67 |
| 2007/0249940 A1* | 10/2007 | Kohno | A61B 1/00082 600/463 |
| 2008/0021269 A1* | 1/2008 | Tinkham | A61B 1/00098 600/104 |
| 2015/0359594 A1* | 12/2015 | Ben-Oren | A61B 18/24 606/3 |

* cited by examiner

*Primary Examiner* — Timothy J Neal
(74) *Attorney, Agent, or Firm* — Ostrolenk Faber LLP

(57) ABSTRACT

An endoscopic instrument includes: a body extending in a lengthwise direction, and having a first channel and a second channel parallel to each other; and an optical portion provided with an incident surface formed at an end part of the first channel so as to receive an external image, the optical portion disposed at the first channel, wherein the second channel is formed such that a laser module is insertable thereinto, and the laser module is configured to output laser in a direction crossing the lengthwise direction, and wherein the incident surface is formed to be inclined from a sectional surface of the first channel, such that the optical portion captures an image disposed on a path of the outputted laser. With such a configuration, a surgery can be performed through a single punched hole.

8 Claims, 7 Drawing Sheets

ENDOSCOPIC INSTRUMENT

BACKGROUND OF THE INVENTION

1. Field of the Invention

This specification relates to an endoscopic instrument used for medical treatment, and more particularly, to an endoscopic instrument for surgery for joints or part around the joints.

2. Background of the Invention

Generally, an endoscopic instrument is more preferred than an open-type surgery apparatus. The reason is because recovery time after surgery and complications are reduced when a wound is small. Accordingly, various endoscopic instruments for surgery, suitable for precise arrangement of an operation portion of an end part thereof at a desired surgical place through a cannular of a trocar, have been developed.

Each of the endoscopic instruments includes a long body between a handle portion manipulated by a clinician, and an operation portion of an end part thereof. The body is formed as a straight line so as to be inserted into a human body, and the operation portion is arranged at the end part of the body so as to be perpendicular to the straight line.

An impingement syndrome, an object to be treated by a joint endoscope, occurs due to a small space by collision and pressure by multiplied soft tissues, and due to pressure and collision by protruded bones or deformed bones. In the past, the impingement syndrome was called frozen shoulders.

In the case of the joint endoscope which treats the impingement syndrome, two holes are punched for surgery because a surgical spot is too small. However, efforts to minimize the number of holes formed at a patient's body, or developments of an apparatus for treating the impingement syndrome more simply are ongoing inactively.

SUMMARY OF THE INVENTION

Therefore, an aspect of the detailed description is to provide an endoscopic instrument capable of preventing tendon rupture prior to rupture due to an impingement syndrome, and capable of performing relief from pain due to collision and improved exercise in a more rapid and simple manner.

Another aspect of the detailed description is to provide a joint endoscopic instrument capable of performing a surgery by punching a single hole.

To achieve these and other advantages and in accordance with the purpose of this specification, as embodied and broadly described herein, there is provided an endoscopic instrument, including: a body extending in a lengthwise direction, and having a first channel and a second channel parallel to each other; and an optical portion provided with an incident surface formed at an end part of the first channel so as to receive an external image, the optical portion disposed at the first channel. The second channel may be formed such that a laser module is insertable thereinto, and the laser module may be configured to output laser in a direction crossing the lengthwise direction. The incident surface may be formed to be inclined from a sectional surface of the first channel, such that the optical portion captures an image disposed on a path of the outputted laser.

According to an embodiment of the present invention, an output surface of the laser module may be formed to face a height direction of the body perpendicular to the lengthwise direction, and the incident surface may be formed to face one point on the path.

The incident surface may be formed on a plane where the output surface of the laser module is tilted based on an axis of the lengthwise direction and an axis of a widthwise direction of the body.

According to another embodiment of the present invention, the output surface of the laser module may protrude more than the incident surface in the lengthwise direction. The first and second channels may be arranged in a widthwise direction of the body perpendicular to the lengthwise direction.

According to another embodiment of the present invention, the second channel may be formed such that a burr module not the laser module is insertable thereinto, and a cutting blade of the burr module may be configured to cut an object which is disposed in a direction crossing the lengthwise direction. The incident surface may be formed to be lower than the output surface of the laser module or the cutting blade of the burr module in a height direction of the body.

According to another embodiment of the present invention, the laser module may be provided with an optical unit for changing a moving direction of the outputted laser in the second channel, such that the laser is output in a direction crossing the lengthwise direction.

According to another embodiment of the present invention, an opening may be formed at an end part of the body, such that the incident surface and the output surface of the laser module are exposed to outside therethrough. The opening may be formed to be open in the height direction and the lengthwise direction of the body, respectively.

To achieve these and other advantages and in accordance with the purpose of this specification, as embodied and broadly described herein, there is also provided an endoscopic instrument having a body formed along an X-axis, wherein the body includes: a first channel where an optical portion for receiving an external image is arranged; and a second channel formed such that a laser module or a burr module is insertable thereinto, formed along the X-axis, and arranged close to the first channel along a Y-axis, and wherein the optical portion is formed to receive an image of an object, in a state where an output surface of the laser module or a cutting blade of the burr module faces the object disposed on a Z-axis.

The present invention can have the following advantages.

Firstly, the endoscopic instrument can perform a surgery through a single punched hole, on a narrow region such as a joint. Accordingly, disadvantages such as a long hospitalization, a surgery under general anesthesia, increased costs and a slow recovery, can be solved.

Secondly, since the laser module and the burr module are replaceable with each other, various surgeries based on a clinician's determination can be performed.

Thirdly, since an image is received in a state where a joint mirror is toward a direction different from an introduction direction of the endoscopic instrument, a surgical scene can be obtained in the same or similar direction as or to the conventional direction, even by the joint mirror integrated with the laser module or the burr module.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Figure 1:
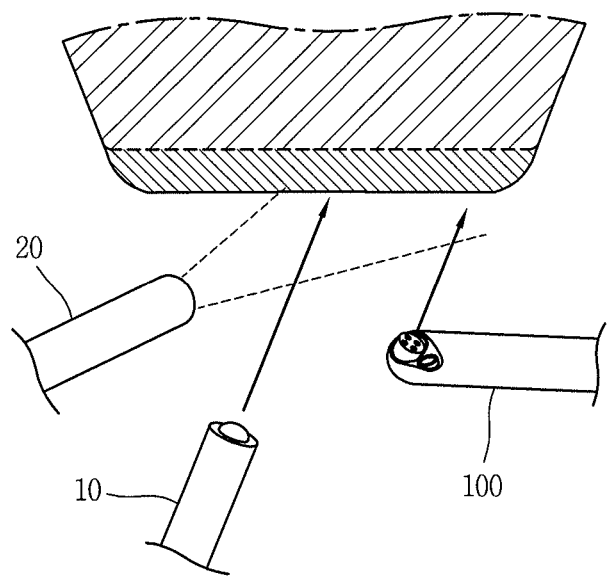
FIG. 1 is a conceptual view illustrating a surgery method according to an embodiment of the present invention.

Description will now be given in detail of preferred configurations of an endoscopic instrument according to the present invention, with reference to the accompanying drawings. The same or similar reference numerals will be provided to the same or similar components as or to components of the aforementioned embodiment, and the same explanations will be omitted.

FIG. 1 is a conceptual view illustrating a surgery method according to an embodiment of the present invention.

Referring to FIG. 1, a laser module (burr module) 10 is introduced to a human body in one direction, and a joint mirror 20 is additionally introduced to the human body in a direction crossing the one direction, thereby capturing a surgical scene. Such a surgery can treat an impingement syndrome. However, such a surgery has a problem in punching two holes at a human body. The endoscopic instrument of the present invention can treat an impingement syndrome by punching a single hole at a human body, as a joint mirror and a laser module are integrated with each other.

However, in the case where the joint mirror and the laser module are integrated with each other, a clinician performs a surgery using the laser module (burr module) at a front side and lateral sides while viewing the joint mirror at a rear side. This may cause the clinician not to utilize his or her accumulated clinical experiences. To solve such a problem, the endoscopic instrument 100 of the present invention is configured so that a clinician can utilize his or her accumulated clinical experiences, with a structure that the joint mirror and the laser module are integrated with each other.

In this case, the endoscopic instrument 100 is introduced to the human body in a different direction from the conventional direction, for surgery. According to the surgery method using the endoscopic instrument, when the joint mirror and the laser module are separately provided, a single hole may be punched. Further, the endoscopic instrument 100 is introduced to the human body in a different path from a path of the joint mirror and the laser module. This is very useful to a narrow spot around the shoulder.

Hereinafter, a structure of the endoscopic instrument 100 applicable to the surgery method will be explained in more detail.

Figure 2:
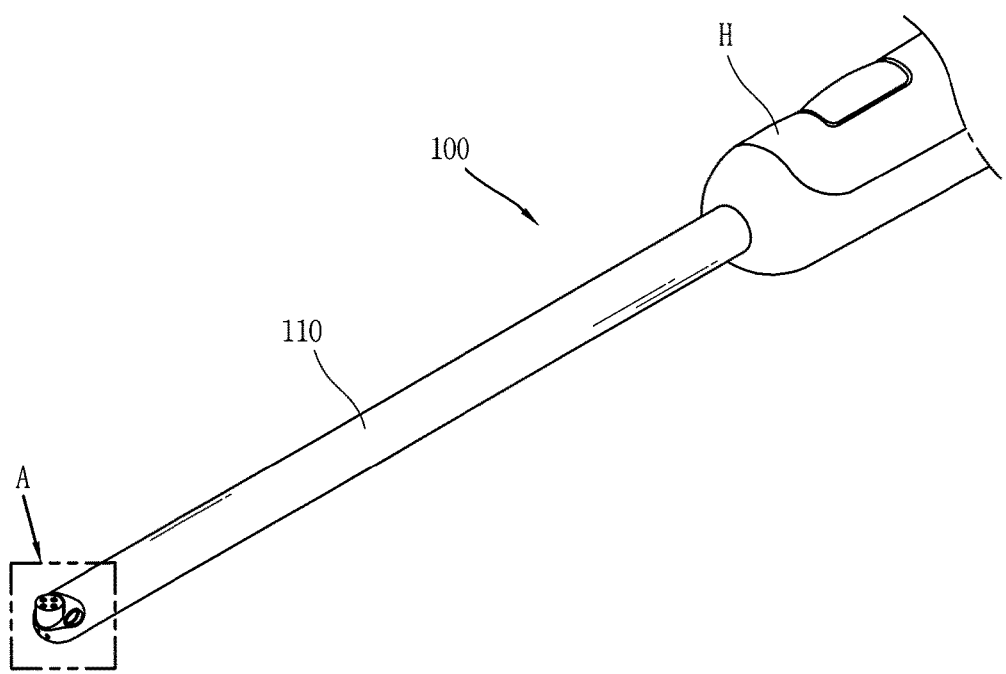
FIG. 2 is a front perspective view of an endoscopic instrument according to the present invention.
Figure 3:
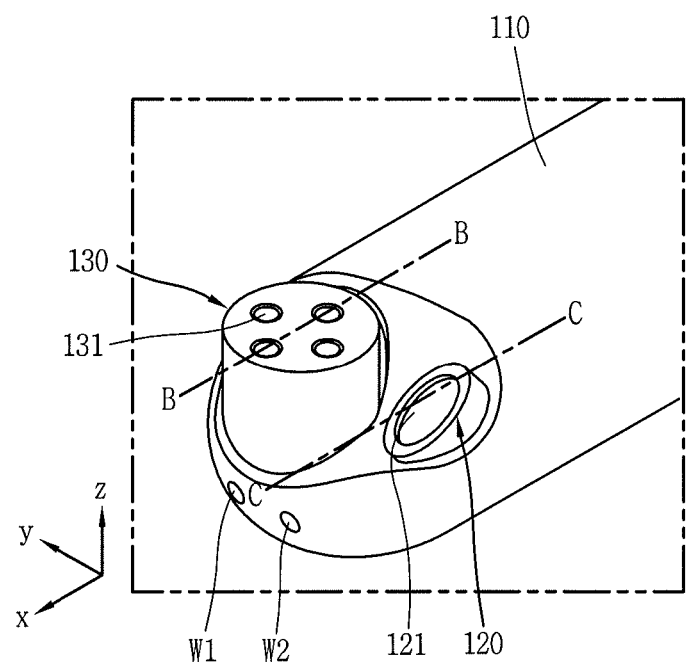
FIG. 3 is an enlarged view of part 'A' in FIG. 2.
Figure 4A:
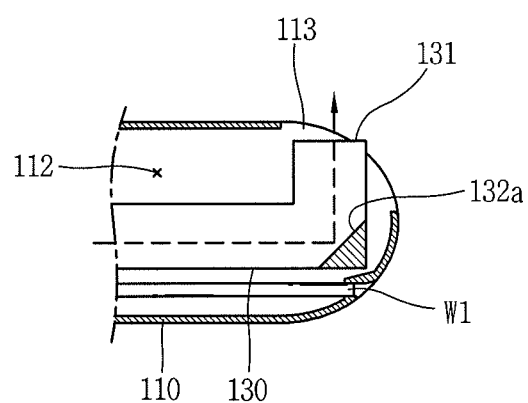
FIGS. 4A and 4C are sectional views taken along lines 'B-B' and 'C-C' in FIG. 3.
Figure 4B:
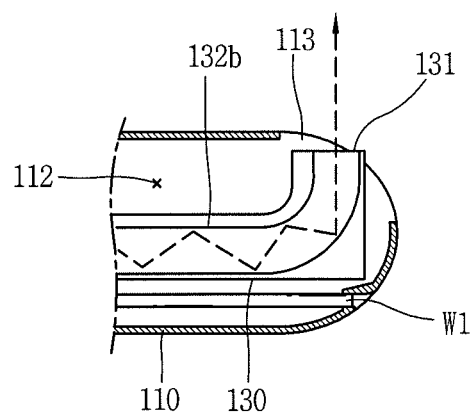
FIG. 4B is a sectional view illustrating a modification example of FIG. 4A.
Figure 4C:
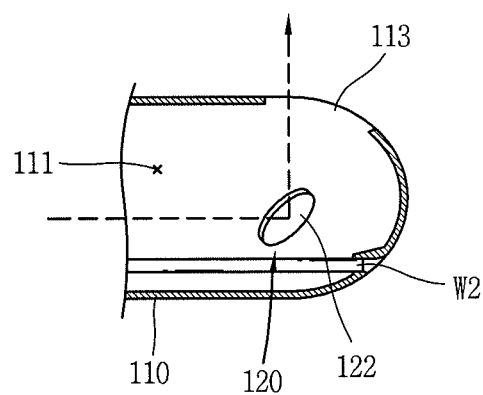
Figure 5:
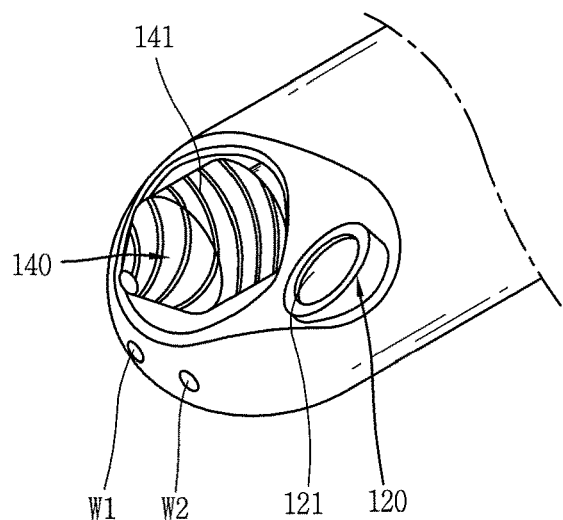
FIG. 5 is a perspective view illustrating a case where a burr module has been amounted to the endoscopic instrument of FIG. 2.

FIG. 2 is a front perspective view of an endoscopic instrument according to the present invention. FIG. 3 is an enlarged view of part 'A' in FIG. 2. FIGS. 4A and 4C are sectional views taken along lines 'B-B' and 'C-C' in FIG. 3. FIG. 4B is a sectional view illustrating a modification example of FIG. 4A. FIG. 5 is a perspective view illustrating a case where a burr module has been amounted to the endoscopic instrument of FIG. 2.

Referring to the drawings, the endoscopic instrument 100 includes a handle portion (H) manipulated by a clinician, a body 110 extending from the handle portion (H) in the form of a straight line, and an operation portion formed at an end part of the body 110.

The body 110 of the endoscopic instrument 100 according to the present invention includes a first channel 111 and a second channel 112.

The first and second channels 111, 112 are partitioned from each other by a partition wall inside the body 110, and are formed in parallel to each other.

More specifically, an optical portion 120 (or joint mirror) for receiving an external image is disposed at the first channel 111, and the second channel 112 is formed so that a laser module 130 or a burr module 140 can be inserted thereinto.

In this case, the body 110 and the first and second channels 111, 112 are long formed in an X-axis direction (lengthwise direction), and the second channel 112 is disposed close to the first channel 111 in a Y-axis direction (widthwise direction). An output surface 131 of the laser module 130, or a cutting blade 141 of the burr module 140 are formed to face an object disposed on a Z-axis. That is, laser is not output in an X-axis direction (introduction direction of the endoscopic instrument 100), but is output in a Z-axis direction (height direction) perpendicular to the X-axis direction.

As shown, the output surface 131 of the laser module 130 may be provided with a plurality of output openings, and the laser module 130 may be formed such that laser is output from each of the output openings. Some of the plurality of output openings may be used for water injection and water suction, not for laser output.

The optical portion 120 is formed to receive an image of an object, in a state where the output surface 131 of the laser module 130 or the cutting blade 141 of the burr module 140 faces the object disposed on a Z-axis.

For instance, the second channel 112 is formed so that the laser module 130 can be inserted thereinto, and the laser module 130 is configured to output laser to a direction crossing the lengthwise direction. Referring to FIG. 4A, the laser module 130 is provided with an optical unit for changing a moving direction of the outputted laser in the second channel 112. The optical unit may be a reflection mirror 132a, a laser optical fiber 132b, etc.

Referring to FIG. 4A, the laser module 130 may be provided with a reflection mirror 132 disposed to reflect the outputted laser in the second channel 112.

For instance, the reflection mirror 132 is disposed to be inclined from a sectional surface of the second channel 112, such that a path of laser, proceeding toward an X-axis direction from an end part of the second channel 112, is changed to a Z-axis direction. FIG. 4B illustrates an example to gradually change a moving path of laser using the laser optical fiber 132b not the reflection mirror 132a.

Referring to FIGS. 2 and 3, the endoscopic instrument 100 includes the optical portion 120. The optical portion 120 is provided with an incident surface 121 formed at an end part of the first channel 111 so as to receive an external image. The incident surface 121 is formed to be inclined from a sectional surface of the first channel 111, such that the optical portion 120 captures an image disposed on a path of the outputted laser. In this case, the first and second channels 111, 112 are arranged to be adjacent to a Y-axis direction, and are formed in parallel to each other.

The optical portion 120 is implemented as an optical system disposed on the first channel 111 so as to receive an external image. The optical system is formed such that an external image received through the incident surface 121 is transmitted along the X-axis direction. FIG. 4C illustrates a reflection mirror 122 disposed at the end of the first channel 111. However, the present invention is not limited to this. For instance, the optical system may be implemented as a refraction and transmission type for changing an optical path through a prism, etc., rather than a reflection type.

More specifically, referring to FIG. 3, the output surface 131 of the laser module 130 is formed to face a height direction (Z-axis direction) of the body 110, and the incident surface 121 is formed to face one point on a path of the outputted laser. Once an object for surgery is disposed on the one point, not only a laser surgery can be performed, but also the optical portion 120 can capture a surgical scene.

For such an operation, the output surface 131 of the laser module 130 is formed to protrude more than the incident surface 121 in the X-axis direction, and the incident surface 121 is formed to be inclined from the output surface 131.

In this case, the incident surface 121 is formed on a plane where the output surface 131 of the laser module 130 is tilted based on the X-axis and the Y-axis, respectively. For instance, the incident surface 121 may be formed on a plane where the output surface 131 has a tilted angle of 70° based on the X-axis, and has a tilted angle of 30° based on the Y-axis. Further, the incident surface 121 of the optical portion 120 is disposed on the left side of the X-axis, and the output surface 131 of the laser module 130 (or cutting blade of the burr module) is disposed on the right side of the X-axis. The incident surface 121 may be formed to be lower than the output surface 131 of the laser module 130 (or cutting blade of the burr module) in the Z-axis direction. With such a configuration, the endoscopic instrument 100 can be manipulated more easily.

As shown, an opening 113 is formed at the end of the body 110, such that the incident surface 121 and the output surface 131 of the laser module 130 are exposed to outside therethrough. The opening 113 is formed such that a predetermined part thereof is open in the X-axis direction and the Z-axis direction, respectively.

In the endoscopic instrument 100 of the present invention, the optical portion 120 disposed at the first channel 111 may be formed as a fixed type, such that a position to which the incident surface 121 faces is always constant. On the contrary, the laser module 130 disposed at the second channel 112 may be formed to be withdrawable to outside from the second channel 112. More specifically, the second channel 112 may be formed so that the burr module 140 rather than the laser module 130 can be inserted thereinto.

However, the present invention is not limited to this. For instance, the optical portion 120 may be formed to be withdrawable to outside from the first channel 111. Further, the incident surface 121 may be formed to be tilted or movable by an external manipulation.

Referring to FIG. 5, the cutting blade 141 of the burr module 140 is configured to cut an object disposed in a direction crossing the lengthwise direction. For instance, the cutting blade 141 may be formed on an outer circumferential surface of the burr module 140. In this case, the end of the burr module 140 may have a conical shape, and the cutting blade 141 may be connected up to the conical end. With such a structure, cutting may be performed with respect to not only an object disposed in a direction crossing the lengthwise direction, but also an object disposed at a front side along the lengthwise direction.

In order for the laser module 130 or the burr module 140 to be operated at the end of the body 110, the partition wall between the first and second channels 111, 112 may be formed to be lower at the end of the body 110. Further, a wall surface of the end of the body 110 may be formed, such that the second channel 112 is lower than the first channel 111. With such a structure, the laser module 130 or the burr module 140 can be operated more smoothly.

Referring to FIGS. 3 and 5, a water injection opening (W1) and a water suction opening (W2) may be provided at a lower part of the end of the body. For instance, the water injection opening (W1) and a passage connected to the water injection opening (W1) may be disposed below the laser module 130, and the water suction opening (W2) and a passage connected to the water suction opening (W2) may be disposed below the optical portion 120. Water is injected into a human body through the water injection opening (W1), and pressure for suction is provided to the water suction opening (W2), such that heat and residue generated during a laser surgery or a bone cutting operation are discharged to outside through the water suction opening (W2). With such a structure, water injected into a human body may be discharged to outside together with heat and residue.

Hereinafter, a surgery method for treating an impingement syndrome using the endoscopic instrument 100 will be explained.

Figure 6:
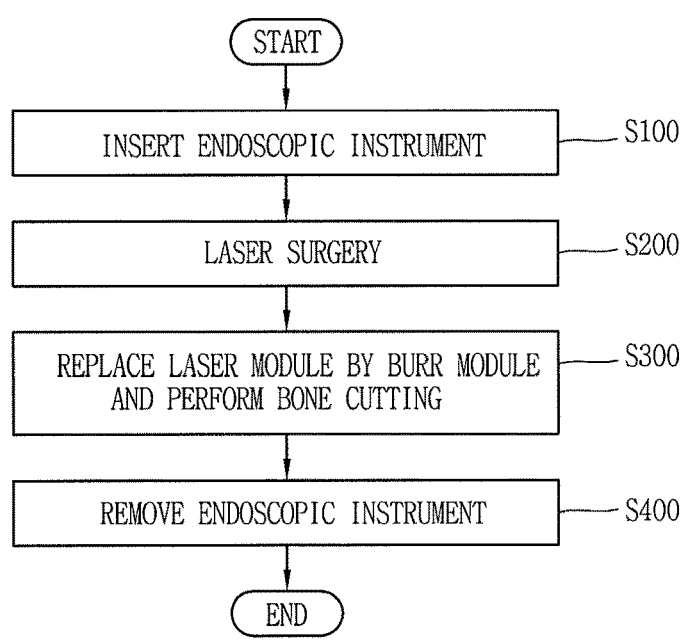
FIG. 6 is a flowchart illustrating a surgery method using the endoscopic instrument of FIG. 2.

FIG. 6 is a flowchart illustrating a surgery method using the endoscopic instrument of FIG. 2.

Firstly, the endoscopic instrument is inserted into a human body (S100). In this case, a single hole is punched, and the body 110 of the endoscopic instrument is inserted into the hole. Then, a laser surgery is performed at a muscle region where an impingement syndrome has occurred, using the laser module 130 (S200). In this case, laser is output in a direction perpendicular to an introduction direction of the body 110, and the optical portion 120 captures a laser surgical region next to the laser module 130.

Then, the endoscopic instrument 100 is taken out of the human body (S400), or the laser module 130 is withdrawn from the endoscopic instrument 100. And the laser module 130 is replaced by the burr module 140, and then a bone cutting operation is performed (S300). In the case of taking the endoscopic instrument 100 out of the human body, a bone cutting operation is not performed, but only a laser surgery is performed for treatment of an impingement syndrome. Alternatively, a new endoscopic instrument mounted with a burr module is inserted into the human body through a preformed hole.

On the other hand, in the case of withdrawing the laser module 130 from the endoscopic instrument 100, the burr module 140 is inserted into a region of the laser module 130, for bone cutting. In this case, the laser module 130 is configured to be inserted into or withdrawn from the second channel. Thus, the burr module 140 may be insertable into the second channel where the laser module has been withdrawn.

According to the surgery method, a laser surgery can be performed exclusively or together with a bone cutting operation, through a single punched hole.

The endoscopic instrument which can implement such a surgery method may be modified in various manners. Hereinafter, such a modification will be explained with reference to FIGS. 7 to 10.

FIGS. 7 to 10 are conceptual views illustrating other embodiments of the present invention.

Figure 7:
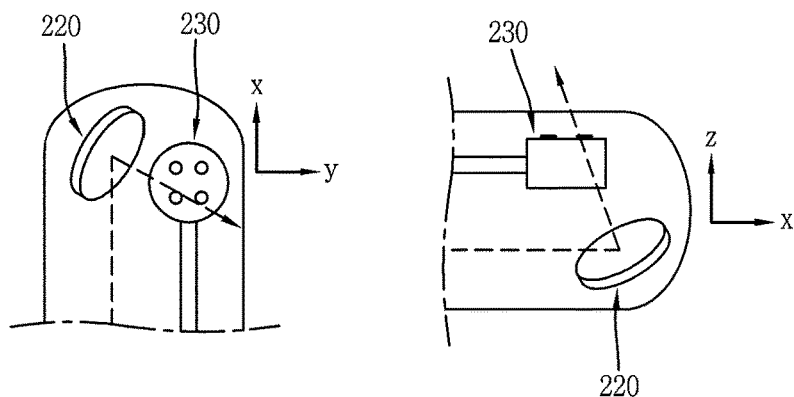
FIGS. 7 to 10 are conceptual views illustrating other embodiments of the present invention.

Referring to FIG. 7, an incident surface of an optical portion 220 is formed to be inclined in an opposite direction to the incident surface of the optical portion 120 aforementioned with reference to FIG. 2. In this case, the incident surface is formed to protrude more than an output surface of a laser module 230 in an X-axis direction.

Figure 8:
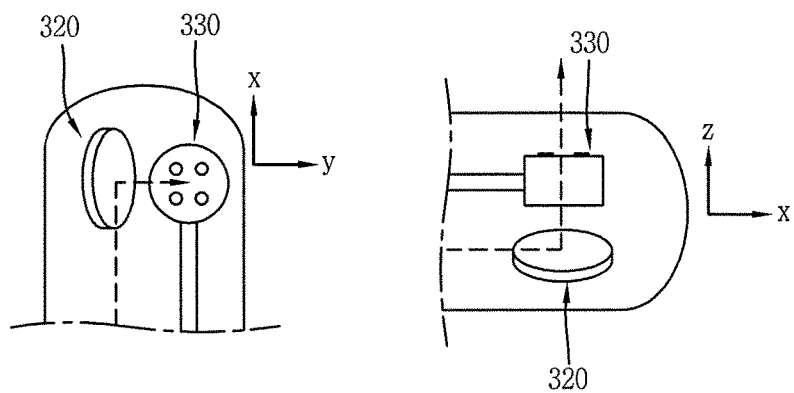

As another example, referring to FIG. 8, an incident surface of an optical portion 320 is disposed on the same position as an output surface of a laser module 330 in an X-axis direction. In this case, the incident surface may be implemented as a surface rotated only in the X-axis direction.

Figure 9:
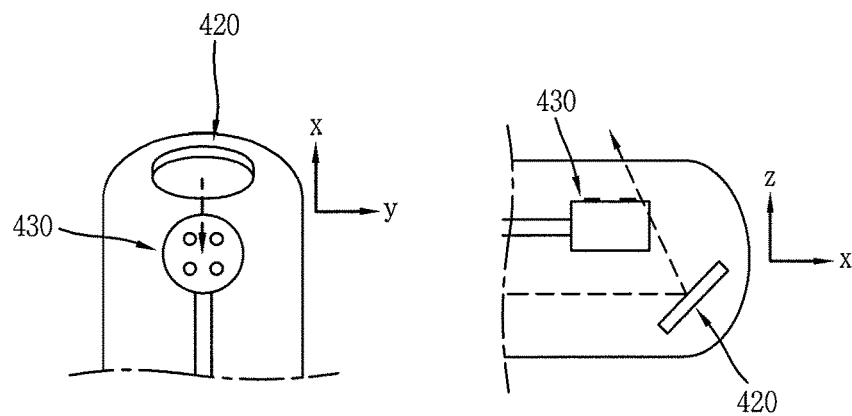

The endoscopic instrument of the present invention may be configured such that the laser module and the optical portion are overlapped with each other in a Z-axis direction. Referring to FIG. 9, an incident surface of an optical portion 420 is formed to protrude more than an output surface of a laser module 430 in an X-axis direction. An opening of a body may not be formed at the end of the body, but may be formed only on an outer circumferential surface of the end.

The optical portion 420 is disposed below the laser module 430. And the incident surface of the optical portion 420 protrudes up to a point where the optical portion 420 is not overlapped with the laser module 430, thereby facing one point on a path of outputted laser. In this case, a partition wall between first and second channels is formed to divide inside of the body in upper and lower directions.

Figure 10:
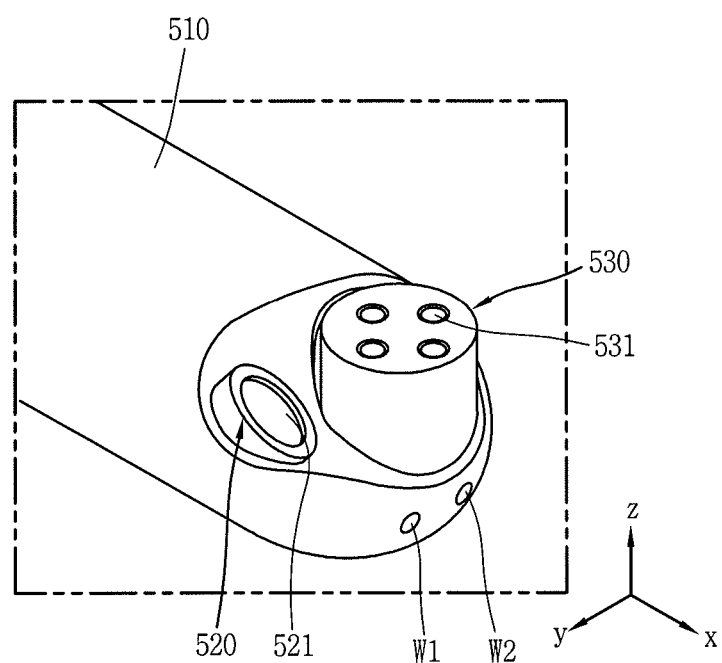

The endoscopic instrument of the present invention may be configured such that positions of the laser module and the optical portion are switched from each other in right and left directions. FIG. 10 illustrates such a case. The same or similar reference numerals will be provided to the same or similar components as or to components of the aforementioned embodiment, and the same explanations will be omitted.

In the aforementioned embodiment, the laser module is disposed on the right side and the optical portion is disposed on the left side based on the X-axis, such that a clinician utilizes his or her accumulated clinical experiences by a method using the laser module (or burr module) on a different position, while viewing a transmitted image using the joint mirror. However, in this embodiment, a laser module 530 is disposed on the left side and an optical portion 520 is disposed on the right side based on an X-axis, for development of a novel surgical method. More specifically, the endoscopic instrument of FIG. 10 may form a pair with the endoscopic instrument 100 of FIG. 2. With such a structure, a clinician can select a position of the laser module and the optical portion, in an optimum manner for surgery for a left object (e.g., left shoulder) or a right object (e.g., right shoulder).

The endoscopic instrument of the present invention is not limited to the aforementioned configuration and method. That is, the endoscopic instrument of the present invention may be also applicable to an industrial purpose or a surgery for other parts of a human body. For instance, the endoscopic instrument of the present invention may be applicable to a neural compression syndrome or a wrist syndrome having a narrow surgical region.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An endoscopic instrument for surgery for joints or parts around the joints, comprising:
 a body extending in a lengthwise direction, and having a first channel and a second channel parallel to each other; and
 an optical portion provided with an incident surface formed at an end part of the first channel so as to receive an external image, the optical portion disposed at the first channel; and
 a laser module configured to output laser in a direction crossing the lengthwise direction; and
 wherein the second channel is formed such that the laser module is insertable thereinto,
 wherein an output surface of the laser module is formed to face a height direction of the body perpendicular to the lengthwise direction,
 wherein the incident surface is spaced apart from the laser module in a widthwise direction of the body,
 wherein the incident surface is formed on a plane that is tilted relative to the output surface of the laser module about an axis of the widthwise direction and an axis of the lengthwise direction of the body so as to face one point of a target object disposed on a path of the output laser.

2. The endoscopic instrument for surgery for joints or parts around the joints of claim 1, wherein the output surface of the laser module protrudes more than the incident surface in the lengthwise direction.

3. The endoscopic instrument for surgery for joints or parts around the joints of claim 2, wherein the first and second channels are arranged in the widthwise direction of the body perpendicular to the lengthwise direction.

4. The endoscopic instrument for surgery for joints or parts around the joints of claim 1, wherein the laser module is provided with an optical unit for changing a moving direction of the outputted laser in the second channel, such that the laser is output in a direction crossing the lengthwise direction.

5. The endoscopic instrument for surgery for joints or parts around the joints of claim 1, wherein an opening is formed at an end part of the body, such that the incident surface and the output surface of the laser module are exposed to outside therethrough.

6. The endoscopic instrument for surgery for joints or parts around the joints of claim 5, wherein the opening is formed such that a predetermined part thereof is open in the height direction and the lengthwise direction of the body, respectively.

7. An endoscopic instrument for surgery for joints or parts around the joints having a body formed along an X-axis,
 wherein the body includes:
 an optical portion for receiving an external image; and a first channel where the optical portion is arranged; and
a laser module configured to output laser; and
a second channel formed such that the laser module is insertable thereinto, formed along the X-axis, and arranged close to the first channel along a Y-axis, and
wherein the laser module is arranged such that an output surface of the laser module faces a target disposed on a Z axis,
wherein the optical unit is spaced apart from the laser module along the Y axis,
wherein the optical unit is tilted about the X-axis and the Y-axis, so as to receive an image of the object facing the laser module.

8. The endoscopic instrument for surgery for joints or parts around the joints of claim 7, wherein an incident surface of the laser module is formed to be inclined from a sectional surface of the first channel, such that the optical portion captures an image disposed on a path of laser outputted from the output surface.

\* \* \* \* \*